United States Patent [19]

Mullin et al.

[11] Patent Number: 4,464,233

[45] Date of Patent: Aug. 7, 1984

[54] PREPARATION OF ADDUCTS WHICH MAY BE USED IN THE PREPARATION OF COMPOUND SEMICONDUCTOR MATERIALS

[75] Inventors: John B. Mullin, West Malvern; Arthur K. Holliday, Bromborough; David J. Cole-Hamilton, Ormskirk; Anthony C. Jones, St. Helens, all of England

[73] Assignee: The Secretary of State for Defense in Her Britannic Majesty's Government of the United Kingdom of Great Britain and Northern Ireland, London, England

[21] Appl. No.: 443,733

[22] Filed: Nov. 22, 1982

[30] Foreign Application Priority Data

Nov. 25, 1981 [GB] United Kingdom ................ 8135592

[51] Int. Cl.$^3$ .............................................. C25C 1/00
[52] U.S. Cl. ............................................ 204/59 QM
[58] Field of Search ................................... 204/59 QM

[56] References Cited

U.S. PATENT DOCUMENTS 3,391,066 7/1968 Braithwaite .................. 204/59 QM

Primary Examiner—John F. Niebling
Attorney, Agent, or Firm—Cushman, Darby & Cushman

[57] ABSTRACT

A method of producing an adduct of an organometallic compound $M^1(R^1)_x$, where $M^1$ is a Group II or Group III metallic element and $R^1)_x$ represents a plurality of organic radicals, which may be the same or different, x being an integer equal to the valency of $M^1$, comprises electrolysing, using a sacrificial anode of the metal $M^1$, a solution containing components A, B and C as follows:

A: a magnesium compound $MgR_2^1$;
B: a readily ionizable support electrolyte providing relatively large anions and cations;
C: a polar aprotic liquid which is a solvent for both components A and B; the metal $M^1$ being selected from the group consisting of: indium, gallium, cadmium.

9 Claims, No Drawings

PREPARATION OF ADDUCTS WHICH MAY BE USED IN THE PREPARATION OF COMPOUND SEMICONDUCTOR MATERIALS

The present invention relates to the preparation of organo-metallic adducts which may be used as intermediates in the preparation of compound semiconductor materials.

Compound semiconductor materials, eg materials such as gallium arsenide, indium phosphide, gallium phosphide and cadmium mercury telluride are well known materials having uses in the electronics industry in such applications as microwave oscillators, semiconductor light emitting diodes and lasers, and infrared detectors.

Such materials have been made in the past by forming, usually on a substrate crystal, one or more active layers, by the method of vapour phase epitaxy (VPE).

It has been known for some time to produce by VPE compound semiconductors of the form $M^A Q^A$ where $M^A$ is Group III element and $Q^A$ is Group V element by reacting a trialkyl of the element $M^A$ with a gaseous compound, eg a hydride, of the Group V element $Q^A$. This method is a suitable method of preparing gallium arsenide from $Ga(CH_3)_3$ and $AsH_3$, for example. However, in the case where $M^A$ is In and $Q^A$ is P unwanted involatile polymers are formed in the reaction of $In(CH_3)_3$ and $PH_3$.

More recently, an approach has been used in the preparation of III-V compounds which in the case of indium phosphide avoids the formation of unwanted polymers. Adducts of trialkyl compounds of both $M^A$ and $Q^A$, ie adducts of the form $M^A(R^A)_x.Q^A(R^B)_x$, where $R^A$ and $R^B$ are metal alkyls (where x=3), have been formed, eg $(CH_3)_3In.P(C_2H_5)_3 In.N(C_2H_5)_3$. These adducts provide a favourable route to the required semiconductor materials because (i) they are very stable in an inert, water-free atmosphere; (ii) they may be easily purified by sublimation or zone refining; and (iii) they may be decomposed pyrolytically at normal pressure to give the required semiconductor material either alone or in the presence of a Group V hydride.

The adducts have in certain cases additionally contained a halogen eg Cl.

The methods of preparation of these adducts which have been used hitherto have involved direct reaction of the appropriate trialkyl of the Group III element with a compound containing the trialkyl of the Group V element. These methods have the disadvantages that trialkyls of Group III elements can themselves be expensive and difficult to prepare, and dangerous to handle, particularly in the case of the trimethyls and triethyls of indium and gallium.

In addition, if such methods are extended to the preparation of II-VI semiconductor compounds and involve the use of a compound containing a halogen species, contamination of the final product by the halogen species is likely to be a problem.

In a copending U.S. patent application Ser. No. 443,734 of even date by the present Applicant there is described a novel method of preparing an adduct suitable for conversion into a compound semiconductor and of formula $M^1(R^1)_x.(Q(R^2)_y)_z$ where $M^1$ is a Group II or Group III metallic element, Q is a Group V or Group VI element which is able to combine with $M^1$ to form the required compound semiconductor, x is an integer equal to the valency of $M^1$, y is an integer equal to the valency of Q, z is an integer equal to 1 or 2 and $(R^1)_x$ and $(R^2)_y$ each represents a plurality of organic radicals which are the same or different radicals, which method is characterised in that a precursor adduct of the form $M^1(R^1)_x.L$ is reacted with a compound $Q(R^2)_y$, the precursor adduct being less stable than the required adduct suitable for conversion into the compound semiconductor, L being a radical which is less electron donating than $Q(R^2)_y$. If x=3, y=3 and z=1. If x=2, z=1 or 2 and yz=2.

The present invention provides a method of preparation suitable for production of the precursor adduct.

According to the present invention a method of producing an adduct of an organometallic compound $M^1(R^1)_x$, where $M^1$ is a Group II or Group III metallic element and $(R^1)_x$ represents a plurality of organic radicals, which may be the same or different, x being an integer equal to the valency of $M^1$, comprises electrolysing, using a sacrificial anode of the metal $M^1$, a solution containing components A, B and C as follows:

A: at least one magnesium compound $Mg(R^1)_2$;

B: a readily ionisable support electrolyte providing relatively large anions and cations;

C: a polar aprotic liquid which is a solvent for both components A and B:

the metal $M^1$ being selected from the group consisting of: indium, gallium, and cadmium.

The groups $R^1$ may for instance be optionally substituted alkyl or aryl radicals.

The groups $R^1$ are preferably alkyl groups having from 1 to 7 carbon atoms, particularly ethyl or methyl.

Preferably, the groups $R^1$ are the same groups.

Preferably the compound $Mg(R^1)_2$, where $R^1$ is preferably methyl or ethyl, is obtained in a pure form by precipitation of a solvento-magnesium halide complex from a Grignard solution.

By "relatively large" anions and cations is meant anions and cations which when combined as a salt have sufficiently low lattice energy to dissolve in the polar aprotic liquid.

The preferred relative molar proportions of components A, B and C are a:b:c respectively where a is between about 1 and about 10, b is about 1 and c is about 400.

The support electrolyte, component B, is preferably a salt providing cations of the form $R_1R_2R_3R_4Z^+$ where Z is a Group V element, preferably N or P, each of $R_1$, $R_2$, $R_3$ and $R_4$ independently represents hydrogen or an organic radical with the proviso that at least two, preferably three and desirably four of $R_1$, $R_2$, $R_3$ and $R_4$ are organic radicals. Preferably $R_1$, $R_2$, $R_2$ and $R_4$ are the same groups and preferably they are alkyl groups having seven or less carbon atoms.

The anion provided by the support electrolyte may be one of the following:

(i) $ClO_4^-$
(ii) $PF_6^-$
(iii) $AsF_6^-$
(iv) $SbF_6^-$

Tetramethylammonium perchlorate and tetraethylammonium perchlorate are preferred as the support electrolyte.

The polar aprotic liquid, component C, may be selected from the following solvents (or mixtures thereof): aliphatic ethers containing between 3 and 12 carbon atoms; eg cyclic aliphatic mono- or poly-ethers such as tetrahydrofuran or dioxan or non-cyclic ethers such as di(n-propyl)ether; N-methyl pyrollidone; acetonitrile; nitromethane and propylene carbonate.

Tetrahydrofuran is preferred as the polar aprotic liquid.

The adduct formed by the method according to the present invention may advantageously be one of the compound $M^1(R^1)_x$ and a radical which may be replaced by a more electron donating radical to form a further, more stable halogen-free adduct suitable for decomposition into a compound semiconductor containing the metal $M^1$.

For instance, the adduct may be an adduct of the compound $M^1(R^1)_x$ and a radical provided by the polar aprotic liquid, component C.

As a preferred example, the adduct may be a 1:1 adduct of tetrahydrofuran and a trialkyl indium or gallium. These adducts are the subject of a copending U.S. patent application Ser. No. 443,734 of even date by the present Applicant. These adducts provide a novel precursor to further more stable adducts in which the tetrahydrofuran radical is replaced by a radical $Q^1(R^3)_3$ where $Q^1$ is a Group V element, eg N, P or As, and $R^3$ is an organic radical eg ethyl or methyl. Such further adducts are preferred to the corresponding basic trialkyl compounds, ie trialkyl indium or gallium, for decomposition into semiconductor compounds of indium and gallium, eg GaAs and InP, because they are safer.

Alternatively, or in addition, the adduct may be formed of $M^1(R^1)_x$ together with a radical derived from the support electrolyte.

For example, where the support electrolyte is a n-butylammonium salt, eg perchlorate, a 1:1 adduct of n-butylamine and the metal compound $M^1(R^1)_x$, eg trimethyl gallium, is formed.

As noted above adducts of compounds $M^1(R^1)_x$ which are adducts of the form $M^1(R^1)_x.Q^1(R^3)_x$ are known and are preferred to the basic compounds $M^1(R^1)_x$ for decomposition into the compound semiconductors $M^1Q^1$. However these adducts have been prepared hitherto directly from the basic compounds $M^1(R^1)_x$ which, as noted above, are themselves expensive and difficult to prepare, and are relatively dangerous. As noted above, the method described in a copending Application provides a route to these adducts from precursor adducts of the form $M^1(R^1)_x.L$ where L is a radical less electron donating than $Q^1(R^3)_x$ thus avoiding use of the compounds $M^1(R^1)_x$.

The present invention unexpectedly provides a preferred way of preparing the precursor adducts $M^1(R^1)_x.L$ which avoids intermediate use of the compounds $M^1(R^1)_x$ and which can be simpler and cheaper than methods used for preparation of the compounds $M^1(R^1)_x$.

Electrolytic methods have previously been used for the preparation of metal alkyls particularly lead tetraethyl, but not for the preparation of adducts thereof; and as noted above it is desirable in any event to avoid formation of the metal alkyls per se.

Embodiments of the present invention will now be described by way of example.

In the following Examples all electrochemical preparations were carried out in an atmosphere of dry oxygen-free nitrogen using a three-necked flask fitted with a water condenser, platinum cathode and an indium or gallium anode (as appropriate). The power supply was a Solartron Vari-Pack, Model SRS 153.

All chemicals and solvents were dried and purified before use by standard methods.

EXAMPLE 1

Preliminary preparation of dimethylmagnesium.

Dimethylmagnesium for use in the following Examples was prepared in a known way by the precipitation of a dioxanmagnesium halide complex from a Grignard solution as follows:

MeMgI was prepared by the slow addition of methyliodide (30 ml, 0.48 moles) to a stirred suspension of magnesium turnings (12.6 g, 0.53 moles) in diethyl ether (500 ml). Addition of dioxan (55 ml, 0.64 moles) precipitated magnesium iodide. The clear supernatent was filtered and the diethyl ether removed in vacuo to leave the white solid dimethylmagnesium from which residual dioxan was removed by heating in vacuo at 130° C.–140° C. for 18 hours.

EXAMPLE 2

Electrolytic preparation of a trimethylgalliumtetrahydrofuran (thf) adduct.

A mixture of dimethylmagnesium (0.9 g, 17 mmole) and tetraethylammonium perchlorate (1.0 g, 4 mmole) in thf (100 ml) was electrolysed using a Pt cathode (1 × 1 cm plate) and a sacrificial gallium pool anode. The mixture was heated to 70° C. and was stirred continuously throughout the electrolysis. A current of 40 mA was obtained at 100 V. The reaction was allowed to proceed for 56 hours during which time the mixture darkened considerably. After cooling, the mixture was allowed to settle and was then filtered. After removal of the thf in vacuo the pure liquid product was obtained by condensing it into a trap at −196° C. in vacuo, whilst the distillation vessel was heated to 60° C.

The product was investigated using:
(i) mass spectra measured on a VG Micromass 12 (Trade Mark) mass spectrometer;
(ii) $^1$H nuclear magnetic resonance (nmr) spectra recorded on a PE R12B (Trade Mark) instrument at 60 MHz;
(iii) Infrared spectroscopy using a PE 577 (Trade Mark) instrument.

The results obtained are as listed in the Tables below.

EXAMPLE 3

Electrolytic preparation of a trimethylindiumtetrahydrofuran adduct.

A mixture of dimethylmagnesium (0.5 g, 10 mmole) and tetraethylammonium perchlorate (1.0 g, 4 mmole) in thf (100 ml) was electrolysed using a Pt cathode and a sacrificial indium wire anode at room temperature (20° C.). A voltage of 100 V was applied and gave a current of 50 mA. The reaction was allowed to proceed for 72 hours during which time magnesium was deposited at the cathode and 1.5 g (10 mmole) of indium was consumed. The mixture was filtered and the thf was removed in vacuo. The pure liquid product was obtained by condensing it into a −196° C. trap in vacuo, whilst the distillation vessel was heated to 60° C.

The product was investigated as in Example 2 and the results obtained are as listed in the Tables below.

EXAMPLE 4

Electrolytic preparation of a trimethylgallium-tributylamine adduct.

A mixture of dimethylmagnesium (2.0 g, 40 mmole) and tetra(n-butyl)ammonium perchlorate (2.0 g, 6 mmole) in thf (100 ml) was electrolysed using a gallium anode and a mixture temperature of 70° C. An applied voltage of 100 V gave a current of 100 mA. After 48 hours the mixture was allowed to cool and settle and was then filtered. Removal of the thf in vacuo left an oil which was purified by condensing it in vacuo into a −196° C. cold trap whilst heating the distillation flask to 60° C. The final product was a low melting point (∼ −15° C.) crystalline compound.

The product was investigated as in Example 2, and also by microanalysis, and the results obtained are as listed in the Tables below.

EXAMPLE 5

Electrolytic preparation of a trimethylindiumtri(n-butyl)amine adduct.

A mixture of dimethylmagnesium (0.2 g, 4 mmole) and tetra(n-butyl)ammonium perchlorate (1.0 g, 3 mmole) in thf (100 ml) was electrolysed at room temperature (20° C.) using an In anode. A voltage of 120 V gave a current of 50 mA. After consumption of 0.3 g (6 mmole) of indium the mixture was filtered and the thf removed in vacuo. The pure product was obtained by vacuum sublimation at 50°-60° C. on to a 15° C. cold finger.

The product was investigated as in Example 2, and also by microanalysis, and the results obtained are as listed in the Tables below.

EXAMPLE 6

Preparation of a dimethyl cadmium adduct.

By electrolysing dimethyl magnesium in tetramethyl ammonium perchlorate and thf using a sacrificial anode of cadmium wire at about 20° C. the adduct $Cd(CH_3)_2 \cdot thf$ may be formed in a similar way to the procedure used in Example 3.

TABLE 1

MASS SPECTRA FOR $M(CH_3)_3$ (ADDUCT) COMPOUNDS
(where Bu = n-butyl)

| Example No. | M | Adduct | m/e (assignment) |
|---|---|---|---|
| 2 | Ga | thf | $69/71[Ga]^+$ $71[C_4H_7O]^+$ $72[C_4H_8O]^+$ $84/86[MeGa]^+$ $99/101[Me_2Ga]^+$ $114/116[Me_3Ga]^+$ $141/143[Ga.thf]^+$ $171/173[Me_2Ga\ thf]^+$ (S = 125° C., I = 13 eV). Batch Inlet |
| 3 | In | thf | $71[C_4H_7O]^+$ $72[C_4H_8O]^+$ $115[In]^+$ $130[MeIn]^+$ $145[Me_2In]^+$ (S = 200° C., I = 30 eV). Solid Probe |
| 4 | Ga | NBu₃ | $69/71[Ga]^+$ $84/86[MeGa]^+$ $86[C_5H_{12}N]^+$ $99/101[Me_2Ga]^+$ $100[GH_{14}N]^+$ $114/116[Me_3Ga]^+$ $142[C_9H_{20}N]^+$ $185[C_{12}H_{27}N]^+$ (S = 90° C., I = 30 eV). Solid Probe |
| 5 | In | NBu₃ | $100[C_6H_{14}N]^+$ $115[In]^+$ $130[MeIn]^+$ $142[C_9H_{20}N]^+$ $145[Me_2In]^+$ $185[C_{12}H_{27}N]^+$ Solid Probe |

(Abbreviations: S = source temperature, I = ionisation energy).
m/e is mass to charge ratio

TABLE 2

$^1$H NMR DATA FOR $M(CH_3)_3$ (ADDUCT) COMPOUNDS
(Bu = n-butyl)

| Example No. | M | Adduct | δ (assignment) |
|---|---|---|---|
| 2 | Ga | thf | 3.6(t, 5H, $\overline{CH_2CH_2CH_2CH_2O}$) |
| | | | 1.6(m, 5H, $CH_2\overline{CH_2CH_2}CH_2O$) |
| | | | −0.3(s, 9H, $Ga(CH_3)_3$) ($d^6$-benzene) |

TABLE 2-continued $^1$H NMR DATA FOR $M(CH_3)_3$ (ADDUCT) COMPOUNDS
(Bu = n-butyl)

| Example No. | M | Adduct | δ (assignment) |
|---|---|---|---|
| 3 | In | thf | 3.5(t, 5H, $\overline{CH_2CH_2CH_2CH_2O}$) |
| | | | 1.5(m, 5H, $CH_2\overline{CH_2CH_2}CH_2O$) |
| | | | 0.0(s, 9H, $In(CH_3)_3$) ($d^8$-toluene) |
| 4 | Ga | NBu₃ | 2.6(t, 6H, $N(\overline{CH_2}CH_2CH_2CH_3)_3$) |
| | | | 1.5(m, 12H, $N(CH_2\overline{CH_2CH_2}CH_3)_3$) |
| | | | 1.0(t, 9H, $N(CH_2CH_2CH_2\overline{CH_3})_3$) |
| | | | −0.1(s, 9H, $Ga(CH_3)_3$) ($d^8$-toluene) |
| 5 | In | Nbu₃ | 2.6(t, 6H, $N(\overline{CH_2}CH_2CH_2CH_3)_3$) |
| | | | 1.5(m, 12H, $N(CH_2\overline{CH_2CH_2}CH_3)_3$) |
| | | | 1.0(t, 9H, $N(CH_2CH_2CH_2\overline{CH_3})_3$) |
| | | | 0.1(s, 9H, $In(CH_3)_3$) ($d^8$-toluene) |

Abbreviations: Bu = n-butyl, thf = tetrahydrofuran, s = singlet, t = triplet, m = multiplet.
δvalues are given in parts per million (ppm) using residual methine proton resonances of benzene (7.3 ppm relative to tetramethyl silane (TMS)) or toluene (7.2 ppm relative to TMS) as a reference.

TABLE 3

INFRARED ABSORPTION SPECTRUM FOR $(CH_3)_3Ga(thf)$ $\nu(cm^{-1})$ Thin film: 2980 (m) 2940 (s) 2890 (m) 1450 (w) 1365 (vw) 1340 (vw) 1250 (br,vw) 1190 (m) 1060 (br,sh,w) 1030 (s) 915 (w) 875 (m) 740 (sh,s) 720 (s) 670 (w) 580 (sh,vw) 550 (vs) 515 (vw)

Abbreviations: vw = very weak, w = weak, m = medium, s = strong, vw = very strong; sh = shoulder; br = broad

TABLE 4

MICROANALYTICAL DATA FOR $M(CH_3)_3$ (ADDUCT) COMPOUNDS

| Example No. | M | Adduct | Microanalysis Found(calculated) | | | |
|---|---|---|---|---|---|---|
| | | | C | H | N | Ga |
| 4 | Ga | NBu₃ | 54.3(60.0) | 11.2(12.0) | 4.4(4.7) | 20.4(23.2) |
| | | | C | H | N | In |
| 5 | In | NBu₃ | 49.1(52.2) | 10.5(10.4) | 3.8(4.1) | 32.8(33.3) |

The above results confirm the structure of the adducts produced in the appropriate Examples. The results are essentially identical to those for the adducts prepared in a known way by adding the appropriate radicals, eg $Ga(CH_3)_3$ and thf, together in stoichiometric amounts.

The precursor adducts produced in Examples 2 and 3 may be converted into final adducts suitable for pyrolytic decomposition into semiconductor compounds as described in a copending U.S. patent application Ser. No. 443,734.

A trialkyl of the Group V element required in the semiconductor may, in excess, be reacted with the precursor adduct at room temperature. For example, $In(CH_3)_3 \cdot thf$ may be reacted with $P(CH_3)_3$ to give $In(CH_3)_3 \cdot P(CH_3)_3$. The final adduct may, for example, be pyrolytically decomposed in the manner described by H. Renz and J. Weidlein in Electronics Letters, Volume 16, Mar. 13, 1980, No. 6, Page 228.

Alternatively, a hydride of the Group V element, eg $PH_3$, may be reacted with the final adduct as in the method described in the article "A new approach to MOCVD of indium phosphide and gallium-indium arsenide" by R. H. Moss and J. S. Evans in J. Crystal Growth, Vol 55 (1981) page 129.

The adducts produced in Examples 4 and 5 may themselves be converted into the compound semiconductors GaN or InN by decomposition, eg in the presence of $NH_3$.

We claim:

1. A method of producing an adduct of an organometallic compound $M^1(R^1)_3$ where $M^1$ is a Group III metallic element selected from indium and gallium and $(R^1)_3$ represents a plurality of alkyl radicals having from 1 to 7 carbon atoms, which radicals may be the same or different, which method comprises electrolysing, using a sacrificial anode of the metal $M^1$, a solution containing components A, B, and C as follows:
   A: at least one magnesium dialkyl compound $Mg(R^1)_2$;
   B: a readily ionisable support electrolyte providing relatively large anions and cations; and
   C: a polar aprotic liquid which is a solvent for both components A and B.

2. A method as claimed in claim 1, wherein the groups $R^1$ in $(R^1)_3$ are the same groups.

3. A method as claimed in claim 2 and wherein the groups $R^1$ are methyl or ethyl groups.

4. A method as claimed in claim 1 and wherein the relative molar proportions of components A, B and C are a:b:c respective where a is between about 1 and about 10, b is about 1 and c is about 400.

5. A method as claimed in claim 1 and wherein the support electrolyte, component B, is a salt providing cations of the form $R_1R_2R_3R_4Z^+$ where Z is a group V element, each of $R_1$, $R_2$, $R_3$ and $R_4$ independently represents hydrogen or an organic radical with the proviso that at lease two of $R_1$, $R_2$, $R_3$ and $R_4$ are radicals.

6. A method as claimed in claim 5 and wherein the anion provided by the support electrolyte is of the following:
   (i) $ClO_4^-$
   (ii) $PF_6^-$
   (iii) $AsF_6^-$
   (iv) (iv) $SbF_6^-$.

7. A method as claimed in claim 6 and wherein the support electrolyte is selected from tetramethylammonium perchlorate and tetraethylammonium perchlorate.

8. A method as claimed in claim 1 and wherein the polar aprotic liquid, component C, is selected from the following solvents or mixtures thereof:
   tetrahydrofuran, dioxan, N-methyl pyrollidone, dipropyl ether, acetonitrile, nitromethane and propylene carbonate.

9. A method as claimed in claim 1 and wherein the adduct formed by the method is a 1:1 adduct of tetrahydrofuran and a trialkyl-indium or -gallium.

* * * * *